US010813867B2

(12) United States Patent
Bebot et al.

(10) Patent No.: US 10,813,867 B2
(45) Date of Patent: *Oct. 27, 2020

(54) COSMETIC COMPOSITION COMPRISING AN AEQUEOUS DISPERSION OF HYDROPHOBIC SILICA AEROGEL PARTICLES AND A PARTICULAR ALCOHOL

(71) Applicant: L'OREAL, Paris (FR)

(72) Inventors: Cecile Bebot, Asnieres (FR); Virginie Masse, Courbevoie (FR); Anne-Sophie Gras, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/410,287

(22) PCT Filed: Jun. 21, 2013

(86) PCT No.: PCT/EP2013/062960
§ 371 (c)(1),
(2) Date: Dec. 22, 2014

(87) PCT Pub. No.: WO2013/190077
PCT Pub. Date: Dec. 27, 2013

(65) Prior Publication Data
US 2015/0320663 A1    Nov. 12, 2015

Related U.S. Application Data

(60) Provisional application No. 61/695,334, filed on Aug. 31, 2012.

(30) Foreign Application Priority Data

Jun. 21, 2012 (FR) ..................... 12 55817

(51) Int. Cl.
A61Q 5/06      (2006.01)
A61K 8/58      (2006.01)
A61K 8/02      (2006.01)
A61K 8/34      (2006.01)
A61K 8/25      (2006.01)
A61K 8/04      (2006.01)

(52) U.S. Cl.
CPC ............ A61K 8/585 (2013.01); A61K 8/0279 (2013.01); A61K 8/04 (2013.01); A61K 8/25 (2013.01); A61K 8/34 (2013.01); A61K 8/345 (2013.01); A61Q 5/06 (2013.01); A61K 2800/26 (2013.01); A61K 2800/30 (2013.01); A61K 2800/412 (2013.01)

(58) Field of Classification Search
None
See application file for complete search history.

(56) References Cited

U.S. PATENT DOCUMENTS

| 2,047,398 | A | 7/1936 | Voss et al. |
| 2,102,113 | A | 12/1937 | Djordjevitch |
| 2,723,248 | A | 11/1955 | Wright |
| 3,211,618 | A | 10/1965 | Kambersky et al. |
| 3,579,629 | A | 5/1971 | Pasero et al. |
| 3,589,978 | A | 6/1971 | Kamal et al. |
| 3,716,633 | A | 2/1973 | Viout et al. |
| 3,734,874 | A | 5/1973 | Kibler et al. |
| 3,779,993 | A | 12/1973 | Kibler et al. |
| 3,810,977 | A | 5/1974 | Levine et al. |

(Continued)

FOREIGN PATENT DOCUMENTS

| DE | 2330956 A1 | 1/1974 |
| DE | 102005052585 A1 | 5/2007 |

(Continued)

OTHER PUBLICATIONS

Dow Corning® VM-2270 Aerogel Fine Particles (Aug. 24, 2012).*
International Search Report and Written Opinion for PCT/EP2013/062960, dated Jul. 16, 2014.
Porter, M.R., "Handbook of Surfactants," Blackie, Glasgow and London, 1991, pp. 116-178.
English abstract of corresponding EP 1190700 for FR 284068, (Mar. 22, 2002).
"Silica Silylate Aerogel for Cosmetic Applications," IP.Com Journal, IP.Com Inc., West Henrietta, NY, XP013112635, Jan. 30, 2006.
International Search Report and Written Opinion of counterpart Application No. PCT/EP2013/062961, dated Dec. 13, 2013.

(Continued)

Primary Examiner — Jyothsna A Venkat
(74) Attorney, Agent, or Firm — The Marbury Law Group, PLLC

(57) ABSTRACT

The present invention relates to a method for the cosmetic treatment of keratin fibres, in particular human keratin fibres such as the hair, characterized in that it consists in applying an effective amount of a cosmetic composition comprising an aqueous dispersion of hydrophobic silica aerogel particles comprising at least one alcohol of formula (I) below, the optical isomers thereof and the solvates thereof, in particular the hydrates thereof: in which formula (I): $R_1$ represents an —OH, —$CH_2OH$ or —$CH_3$ group; $R_2$ represents a hydrogenatom or an —OH group; $R_3$ represents a hydrogen atom, a —$CH_2OH$ group, an —(O—$CH_2$—$CH_2$)n-OH group with n denoting an integer ranging from 1 to 10, a —($CH_2$—$CH_2$)$_n$—OH group with n denoting an integer ranging from 1 to 5 or a —CH(OH)—$CH_3$ group, 20 the formula comprising at least one hydroxyl group.

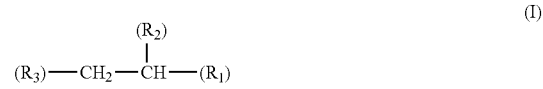

2 Claims, No Drawings

(56) References Cited

U.S. PATENT DOCUMENTS

| | | | |
|---|---|---|---|
| 3,836,537 A | 9/1974 | Boerwinkle et al. | |
| 3,910,862 A | 10/1975 | Barabas et al. | |
| 3,925,542 A | 12/1975 | Viout et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,031,307 A | 6/1977 | DeMartino et al. | |
| 4,119,680 A | 10/1978 | Vachon | |
| 4,128,631 A | 12/1978 | Lundmark et al. | |
| 4,129,711 A | 12/1978 | Viout et al. | |
| 4,131,576 A | 12/1978 | Iovine et al. | |
| 4,137,208 A | 1/1979 | Elliott | |
| 4,165,367 A | 8/1979 | Chkrabarti | |
| 4,223,009 A | 9/1980 | Chakrabarti | |
| 4,282,203 A | 8/1981 | Jacquet et al. | |
| 4,289,752 A | 9/1981 | Mahieu et al. | |
| 4,300,580 A | 11/1981 | O'Neill et al. | |
| 4,693,935 A | 9/1987 | Mazurek | |
| 4,728,571 A | 3/1988 | Clemens et al. | |
| 4,972,037 A | 11/1990 | Garbe et al. | |
| 4,973,656 A | 11/1990 | Blount | |
| 5,660,816 A | 8/1997 | Adams et al. | |
| 5,662,893 A | 9/1997 | George et al. | |
| 5,674,479 A | 10/1997 | George et al. | |
| 5,714,135 A | 2/1998 | Lee et al. | |
| 6,106,813 A | 8/2000 | Mondet et al. | |
| 6,166,093 A | 12/2000 | Mougin et al. | |
| 6,274,152 B1 | 8/2001 | Brieva et al. | |
| 6,319,959 B1 | 11/2001 | Mougin et al. | |
| 6,372,876 B1 | 4/2002 | Kim et al. | |
| 6,395,265 B1 | 5/2002 | Mougin et al. | |
| 7,063,834 B2 | 6/2006 | Mougin et al. | |
| 7,470,725 B2 | 12/2008 | Schwertfeger et al. | |
| 8,021,651 B2 | 9/2011 | Hentrich et al. | |
| 2002/0037256 A1 | 3/2002 | Nocerino et al. | |
| 2002/0150546 A1 | 10/2002 | Mougin et al. | |
| 2003/0191271 A1 | 10/2003 | Mondet et al. | |
| 2004/0180069 A1 | 9/2004 | Bleuez et al. | |
| 2008/0233071 A1 | 9/2008 | Hentrich et al. | |
| 2009/0061004 A1* | 3/2009 | Birkel | A61K 8/046 424/489 |
| 2009/0105353 A1 | 4/2009 | Lorant | |
| 2010/0209376 A1 | 8/2010 | Richters et al. | |
| 2011/0300092 A1 | 12/2011 | Kambach et al. | |
| 2013/0210694 A1 | 8/2013 | Palla-Venkata et al. | |
| 2013/0337026 A1 | 12/2013 | Cassin et al. | |
| 2015/0320663 A1 | 11/2015 | Bebot et al. | |

FOREIGN PATENT DOCUMENTS

| | | | |
|---|---|---|---|
| DE | 102005060435 A1 | 6/2007 | |
| DE | 102007052391 A1 | 5/2009 | |
| DE | 102007053616 A1 | 5/2009 | |
| EP | 0412704 A2 | 2/1991 | |
| EP | 0412707 A1 | 2/1991 | |
| EP | 0582152 A2 | 2/1994 | |
| EP | 0619111 A1 | 10/1994 | |
| EP | 0637600 A1 | 2/1995 | |
| EP | 0640105 A1 | 3/1995 | |
| EP | 0648485 A1 | 4/1995 | |
| EP | 0656021 A1 | 6/1995 | |
| EP | 0751162 A1 | 1/1997 | |
| EP | 1457191 A2 | 9/2004 | |
| EP | 2248513 A1 | 11/2010 | |
| FR | 1222944 A | 6/1960 | |
| FR | 1400366 A | 5/1965 | |
| FR | 1564110 A | 4/1969 | |
| FR | 1580545 A | 9/1969 | |
| FR | 2077143 A | 10/1971 | |
| FR | 2265781 A1 | 10/1975 | |
| FR | 2265782 A1 | 10/1975 | |
| FR | 2350384 A1 | 12/1977 | |
| FR | 2357241 A2 | 2/1978 | |
| FR | 2393573 A1 | 1/1979 | |
| FR | 2439798 A1 | 5/1980 | |
| FR | 2743297 A1 | 7/1997 | |
| FR | 2814068 A1 | 3/2002 | |
| GB | 839805 A | 6/1960 | |
| GB | 922457 A | 4/1963 | |
| GB | 1021400 A | 3/1966 | |
| GB | 1331819 A | 9/1973 | |
| GB | 1572626 A | 7/1980 | |
| JP | 2011-246352 A | 12/2011 | |
| LU | 75370 A1 | 2/1978 | |
| LU | 75371 A1 | 2/1978 | |
| WO | 93/23009 A1 | 11/1993 | |
| WO | 93/23446 A2 | 11/1993 | |
| WO | 94/03510 A1 | 2/1994 | |
| WO | 95/00578 A1 | 1/1995 | |
| WO | 95/18191 A1 | 7/1995 | |
| WO | 97/08261 A1 | 3/1997 | |
| WO | 97/20899 A1 | 6/1997 | |
| WO | 01/45651 A1 | 6/2001 | |
| WO | 2005/070374 A1 | 8/2005 | |
| WO | 2007/051511 A1 | 5/2007 | |
| WO | 2009/059869 A2 | 5/2009 | |
| WO | 2010/054980 A1 | 5/2010 | |
| WO | 2011/148328 A2 | 12/2011 | |
| WO | 2013/190078 A2 | 12/2013 | |
| WO | 2013/190080 A2 | 12/2013 | |

OTHER PUBLICATIONS

International Search Report and Written Opinion of counterpart Application No. PCT/EP2013/062964, dated Jun. 21, 2013.
Non-Final Office Action for co-pending U.S. Appl. No. 14/410,298, dated Mar. 18, 2016.
Non-Final Office Action for co-pending U.S. Appl. No. 14/410,265, dated Nov. 20, 2015.
Final Office Action for co-pending U.S. Appl. No. 14/410,265, dated Mar. 25, 2016.
Final Office Action for copending U.S. Appl. No. 14/410,298, dated Dec. 5, 2016.
Non-Final Office Action for copending U.S. Appl. No. 14/410,265, dated Feb. 16, 2017.
Non-Final Office Action for copending U.S. Appl. No. 14/410,298, dated Feb. 12, 2018.
Final Office Action for copending U.S. Appl. No. 14/410,265, dated Aug. 11, 2017.
Non-Final Office Action for copending U.S. Appl. No. 14/410,265, dated Mar. 30, 2018.
Final Office Action for copending U.S. Appl. No. 14/410,298, dated Sep. 26, 2018.
Final Office Action for co-pending U.S. Appl. No. 14/410,265, dated Dec. 14, 2018.
Non-Final Office Action for co-pending U.S. Appl. No. 14/410,265, dated Apr. 11, 2019.
Non-Final Office Action for co-pending U.S. Appl. No. 14/410,298, dated Apr. 5, 2019.
Final Office Action for co-pending U.S. Appl. No. 14/410,265, dated Aug. 8, 2019.
Final Office Action for co-pending U.S. Appl. No. 14/410,298, dated Sep. 12, 2019.
Non-Final Office Action for copending U.S. Appl. No. 14/410,298, dated Apr. 2, 2020.
Co-pending U.S. Appl. No. 16/363,476, "Cosmetic Composition Comprising Hydrophobic Silica Aerogel Particles and a Fixing Polymer," Inventors: Cécile Bebot et al., filed Mar. 25, 2019.
Non-Final Office Action for copending U.S. Appl. No. 16/363,476, dated Jun. 23, 2020.

* cited by examiner

COSMETIC COMPOSITION COMPRISING AN AEQUEOUS DISPERSION OF HYDROPHOBIC SILICA AEROGEL PARTICLES AND A PARTICULAR ALCOHOL

CROSS REFERENCE TO RELATED APPLICATIONS

This is a national stage application of PCT/EP2013/062960, filed internationally on Jun. 21, 2012, which claims priority to U.S. Provisional Application No. 61/695,334, filed on Aug. 31, 2012, as well as French Appliction No. 1255817, filed Jun. 21, 2012, which are incorporated herein by reference in their entireties.

The present invention relates to a cosmetic composition comprising a dispersion of hydrophobic silica aerogel particles in an aqueous phase comprising at least one particular alcohol, to a method for the cosmetic treatment of keratin fibres using such composition, and also to the use of such a composition for hair treatment, especially for treating keratin fibres and in particular for form retention/shaping of the hair.

In the field of hairstyling, in particular among the hair products intended for shaping and/or form retention of the hairstyle, the hair compositions generally consist of a solution, usually an alcoholic or aqueous solution, and of one or more fixing polymers as a mixture with various cosmetic adjuvants.

These compositions may in particular be in the form of hair gels or mousses that are generally applied to wet hair before blow drying or drying.

It is known to use texturizing products in hair treatment compositions in order to provide body, density and a particular hair shaping. Use is for example made, as texturizing agent, of powders that are incorporated into water or into oil. Mention may in particular be made of applications FR2814067 and FR2814068 that use alumina.

However, certain texturizing powders are not very miscible with water and the composition obtained does not have an acceptable appearance, usually with a dry feel on fibres. Moreover, when they are incorporated into oils, this may lead to a feeling of greasiness and heaviness on the hair. Finally, compositions with powders may sometimes generate residues after mechanical removal or after washing.

There is therefore a real need to have a cosmetic composition that has good styling and cosmetic properties, and that makes it possible to overcome the drawbacks mentioned above.

The applicant has discovered that by combining hydrophobic silica aerogel particles and a particular alcohol it is possible to obtain homogeneous and opalescent mixtures with a pleasant feel, neither dry nor greasy, that do not result in visible residues after removal.

One subject of the present invention is therefore a method for the cosmetic treatment of keratin fibres, in particular human keratin fibres such as the hair, characterized in that it comprises the step of applying an effective amount of a cosmetic composition comprising an aqueous dispersion of hydrophobic silica aerogel particles comprising at least one alcohol of formula (I) below, the optical isomers thereof and the solvates thereof, in particular the hydrates thereof:

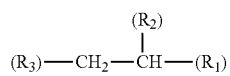

(I)

in which formula (I):
R$_1$ represents an —OH, —CH$_2$OH or —CH$_3$ group;
R$_2$ represents a hydrogen atom or an —OH group;
R$_3$ represents a hydrogen atom, a —CH$_2$OH group, an —(O—CH$_2$—CH$_2$)$_n$—OH group with n denoting an integer ranging from 1 to 10, a —(CH$_2$—CH$_2$)$_n$—OH group with n denoting an integer ranging from 1 to 5 or a —CH(OH)—CH$_3$ group,
the formula (I) comprising at least one hydroxyl group.

The method according to the present invention is used for the cosmetic treatment of keratin fibres, in particular for form retention and/or shaping of the keratin fibres.

The invention also relates to a cosmetic composition as defined above for styling and conditioning keratin fibres, in particular for styling keratin fibres, in particular human keratin fibres such as the hair.

Another subject of the invention is the use of a composition as defined previously for hair treatment, especially for treating keratin fibres and in particular for form retention/shaping of the hair.

Other subjects, features, aspects and advantages of the invention will emerge even more clearly from reading the description and examples which follow.

The composition used in the invention comprises a dispersion of hydrophobic silica aerogel particles in an aqueous phase.

The composition comprises water, preferably in a content of greater than or equal to 5% by weight, relative to the total weight of the composition. The water content varies preferentially from 5% to 90%, preferably from 10% to 90% and better still from 30% to 80% by weight relative to the total weight of the composition.

Preferably, the composition of the invention comprises less than 10% of oil(s), better still less than 5% of oil(s). In one preferred variant of the invention it does not comprise any oil(s).

The composition used in the present invention thus comprises hydrophobic silica aerogel particles.

Aerogels are ultralight porous materials which were first produced by Kristler in 1932.

They are generally synthesized by a sol-gel process in a liquid medium and then dried by extraction with a supercritical fluid. The supercritical fluid most commonly used is supercritical CO$_2$. This type of drying makes it possible to avoid shrinkage of the pores and of the material.

Other types of drying also make it possible to obtain porous materials starting from gel, namely (i) drying by freeze drying, which consists in solidifying the gel at low temperature and in then subliming the solvent, and (ii) drying by evaporation. The materials thus obtained are referred to respectively as cryogels and xerogels. The sol-gel process and the various drying operations are described in detail in Brinker C. J. and Scherer G. W., Sol-Gel Science, New York, Academic Press, 1990.

The expression "hydrophobic silica" is understood to mean any silica, the surface of which is treated with sylilating agents, for example halogenated silanes such as alkylchlorosilanes, siloxanes, in particular dimethylsiloxanes such as hexamethyldisiloxane, or silazanes, so as to functionalize the OH groups with Si—Rn silyl groups, for example trimethylsilyl groups.

Preferably, the hydrophobic aerogel particles that may be used in the present invention advantageously have a specific surface area per unit of mass (SM) ranging from 500 to 1500 m$^2$/g, preferably from 600 to 1200 m$^2$/g and better still from 600 to 800 m$^2$/g.

Preferably, the hydrophobic aerogel particles that may be used in the present invention advantageously have an oil absorption capacity, measured at the wet point, ranging from 5 to 18 ml/g of particles, preferably from 6 to 15 ml/g and better still from 8 to 12 ml/g.

Preferably, the hydrophobic aerogel particles that may be used in the present invention advantageously have a size, expressed as the mean diameter (D[0.5]), of less than 1500 µm, preferably ranging from 1 to 30 µm, preferably from 5 to 25 µm, better still from 5 to 20 µm and even better still from 5 to 15 µm.

The hydrophobic aerogel particles used in the present invention may advantageously have a tapped density $\rho$ ranging from 0.04 g/cm$^3$ to 0.10 g/cm$^3$ and preferably from 0.05 g/cm$^3$ to 0.08 g/cm$^3$.

Preferably, the hydrophobic aerogel particles used in the present invention have a specific surface area per unit of volume SV ranging from 5 to 60 m$^2$/cm$^3$, preferably from 10 to 50 m$^2$/cm$^3$ and better still from 15 to 40 m$^2$/cm$^3$.

According to one preferred embodiment, the hydrophobic aerogel particles according to the invention have a specific surface area per unit of mass (SM) ranging from 500 to 1500 m$^2$/g, preferably from 600 to 1200 m$^2$/g and better still from 600 to 800 m$^2$/g, a size expressed as the mean diameter (D[0.5]) ranging from 1 to 30 µm and/or an oil absorption capacity measured at the wet point ranging from 5 to 18 ml/g of particles, preferably from 6 to 15 ml/g and better still from 8 to 12 ml/g.

According to another advantageous embodiment, the hydrophobic aerogel particles used in the present invention have a specific surface area per unit of mass (SM) ranging from 600 to 800 m$^2$/g and a size, expressed as the volume mean diameter (D[0.5]), ranging from 5 to 20 µm and better still from 5 to 15 µm.

The specific surface area per unit of mass can be determined by the nitrogen absorption method, known as the BET (Brunauer-Emmet-Teller) method, described in The Journal of the American Chemical Society, Vol. 60, page 309, February 1938, which corresponds to international standard ISO 5794/1 (appendix D). The BET specific surface area corresponds to the total specific surface area of the particles under consideration.

The absorption capacity measured at the wet point, denoted Wp, corresponds to the amount of oil which needs to be added to 100 g of particles in order to obtain a homogeneous paste.

It is measured according to the "wet point" method or the method for determining the oil uptake of a powder according to the principle described in standard NF T 30-022. It corresponds to the amount of oil adsorbed onto the available surface of the powder and/or absorbed by the powder by measuring the wet point, described below:

An amount m=2 g of powder is placed on a glass plate and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added at the rate of one drop at a time and the mixture is subsequently triturated with the spatula. The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/m.

The sizes of the aerogel particles according to the invention can be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

In the context of the present invention, this density can be assessed according to the following protocol, known as tapped density protocol:

40 g of powder are poured into a graduated measuring cylinder and then the measuring cylinder is placed on a Stav 2003 device from Stampf Volumeter. The measuring cylinder is subsequently subjected to a series of 2500 tapping actions (this operation is repeated until the difference in volume between two consecutive tests is less than 2%) and then the final volume Vf of tapped powder is measured directly on the measuring cylinder.

The tapped density is determined by the ratio: mass (m)/Vf, in this instance 40/Vf (Vf being expressed in cm$^3$ and m in g).

The specific surface area per unit of volume is given by the relationship:

$$SV = SM \ast \rho$$

where $\rho$ is the tapped density expressed in g/cm$^3$ and SM is the specific surface area per unit of mass expressed in m$^2$/g, as defined above.

The hydrophobic silica aerogel particles used according to the present invention are preferably silylated silica (INCI name: silica silylate) aerogel particles.

The preparation of hydrophobic silica aerogel particles modified at the surface by silylation is further described in document U.S. Pat. No. 7,470,725.

Use will in particular be made of hydrophobic silica aerogel particles surface-modified with trimethylsilyl groups.

As hydrophobic silica aerogels that may be used in the invention, an example that may be mentioned is the aerogel sold under the name VM-2260 (INCI name: Silica silylate), by the company Dow Corning, the particles of which have a mean size of about 1000 microns and a specific surface area per unit of mass ranging from 600 to 800 m$^2$/g.

Mention may also be made of the aerogels sold by Cabot under the references Aerogel TLD 201, Aerogel OGD 201 and Aerogel TLD 203, Enova Aerogel MT 1100 and Enova Aerogel MT 1200.

Use will be made more particularly of the aerogel sold under the name VM-2270 (INCI name: Silica silylate), by the company Dow Corning, the particles of which have a mean size ranging from 5 to 15 microns and a specific surface area per unit of mass ranging from 600 to 800 m$^2$/g.

The hydrophobic silica aerogel particles may be used in a content ranging from 0.05% to 10% by weight, more preferentially from 0.1% to 5% by weight and more preferentially still from 0.5% to 4% by weight relative to the total weight of the composition containing them.

The composition also comprises at least one alcohol of formula (I) below, the optical isomers thereof and the solvates thereof, in particular the hydrates thereof:

in which formula (I):
R₁ represents an —OH, —CH$_2$OH or —CH$_3$ group;
R₂ represents a hydrogen atom or an —OH group;
R₃ represents a hydrogen atom, a —CH$_2$OH group, an —(O—CH$_2$—CH$_2$)$_n$—OH group with n denoting an integer ranging from 1 to 10, a —(CH$_2$—CH$_2$)$_n$—OH group with n denoting an integer ranging from 1 to 5 or a —CH(OH)—CH$_3$ group, the formula comprising at least one hydroxyl group.

The alcohol of formula (I) is preferably a monoalcohol or a dialcohol.

Preferably, the alcohol of formula (I) is selected from ethanol, isopropanol, propylene glycol, 1,4-butylene glycol, 1,3-butylene glycol and PEG 8.

In one preferred variant of the invention, R₃ represents a hydrogen atom or a —CH$_2$OH group.

The alcohol of formula (I) is more preferably chosen from ethanol, isopropanol and propylene glycol.

The alcohol(s) of formula (I) may be present in a content ranging from 1% to 80%, more preferably from 5% to 70% and better still from 10% to 60% by weight relative to the total weight of the composition.

Preferably, the alcohol(s) of formula (I)/hydrophobic silica aerogel particles weight ratio varies from 1 to 100, better still from 5 to 50.

According to a specific embodiment, the composition comprises an aqueous dispersion of hydrophobic silica aerogel particles comprising at least one alcohol of formula (I) below, the optical isomers thereof and the solvates thereof, in particular the hydrates thereof:

(I)

in which formula (I):
R₁ represents an —OH, —CH$_2$OH or —CH$_3$ group;
R₂ represents a hydrogen atom or an —OH group;
R₃ represents a hydrogen atom, a —CH$_2$OH group, an —(O—CH$_2$—CH$_2$)$_n$—OH group with n denoting an integer ranging from 1 to 10, a —(CH$_2$—CH$_2$)$_n$—OH group with n denoting an integer ranging from 1 to 5 or a —CH(OH)—CH$_3$ group,
the formula comprising at least one hydroxyl group,
in which the alcohol(s) of formula (I) is (are) present in the composition in concentrations ranging from 10% to 80%.

The cosmetic composition used in the invention may optionally comprise one or more surfactants that may be selected from anionic, cationic, nonionic, amphoteric or zwitterionic surfactants and mixtures thereof.

Preferably, the surfactant(s) is (are) selected from nonionic surfactants.

The nonionic surfactants that can be used in the compositions of the present invention are compounds that are well known per se (see in particular in this respect "Handbook of Surfactants" by M. R. Porter, published by Blackie & Son (Glasgow and London), 1991, pp. 116-178). They are selected in particular from polyethoxylated, polypropoxylated or polyglycerolated fatty alcohols, polyethoxylated, polypropoxylated or polyglycerolated α-diols, or polyethoxylated, polypropoxylated or polyglycerolated (C$_{1-20}$) alkylphenols, the fatty chain comprising, for example, from 8 to 18 carbon atoms, it being possible for the number of ethylene oxide or propylene oxide groups to range in particular from 1 to 100 and for the number of glycerol groups to range in particular from 1 to 30.

Mention may also be made of condensates of ethylene oxide and of propylene oxide with fatty alcohols; polyethoxylated fatty amides preferably having from 1 to 100 ethylene oxide units, polyglycerolated fatty amides comprising on average from 1 to 5, and in particular from 1.5 to 4 glycerol groups, ethoxylated fatty acid esters of sorbitan having from 1 to 50 ethylene oxide units, fatty acid esters of sucrose, fatty acid esters of polyethylene glycol, alkyl polyglycosides, polyethoxylated plant oils preferably having from 1 to 100 ethylene oxide units, N—(C$_{6-24}$ alkyl)glucamine derivatives or amine oxides, such as (C$_{10-14}$ alkyl) amine oxides or N—(C$_{10-14}$ acyl)aminopropylmorpholine oxides.

The alkyl polyglucosides may be selected, for example, from decyl glucoside ((C$_9$/C$_{11}$ alkyl) (1,4) polyglucoside), such as the product sold under the name Mydol 10® by the company Kao Chemicals or the product sold under the name Plantacare 2000 UP® by the company Henkel and the product sold under the name Oramix NS 10® by the company SEPPIC; caprylyl/capryl glucoside, such as the product sold under the name Plantacare KE 3711® by the company Cognis or Oramix CG 110® by the company SEPPIC; lauryl glucoside, such as the product sold under the name Plantacare 1200 UP® by the company Henkel or Plantaren 1200 N® by the company Henkel; coco glucoside, such as the product sold under the name Plantacare 818 UP® by the company Henkel; caprylyl glucoside, such as the product sold under the name Plantacare 810 UP® by the company Cognis; and mixtures thereof.

When it comprises surfactant(s), the composition comprises one or more surfactants in a content ranging from 0.01% to 10% by weight, preferably in a content ranging from 0.1% to 5% by weight, relative to the total weight of the composition.

The composition used in the invention may also comprise one or more thickeners that can be selected from polymeric thickeners which are natural or synthetic, anionic, amphoteric, zwitterionic, nonionic or cationic and associative or non-associative, and non-polymeric thickeners, such as, for example, an electrolyte.

Mention may be made, as polymeric thickeners, for example, of cellulose thickeners, for example hydroxyethyl cellulose, hydroxypropyl cellulose and carboxymethyl cellulose, guar gum and its derivatives, for example hydroxypropyl guar, sold by the company Rhodia under the reference Jaguar HP 105, gums of microbial origin, such as xanthan gum and scleroglucan gum, carrageenan, for example the carrageenan powder sold by the company Cargill under the reference Satiagum UTC 30, synthetic polymeric thickeners, resulting from radical polymerization reactions or polycondensation reactions such as crosslinked homopolymers of acrylic acid or of acrylamidopropanesulfonic acid, for example Carbomer, or nonionic, anionic or amphoteric associative polymers, such as the polymers sold under the names Pemulen TR1 or TR2 by the company Goodrich, Salcare SC90 by the company Allied Colloids, Aculyn 22, 28, 33, 44 or 46 by the company Rohm & Haas and Elfacos T210 and T212 by the company Akzo or else sodium polyacrylate such as the product sold by the company Sensient under the commercial reference Covacryl MV 60.

When it comprises thickener(s), the composition comprises one or more thickeners, preferably polymeric thickeners, in a content ranging from 0.1% to 10% by weight, preferably in a content ranging from 0.2% to 5% by weight, relative to the total weight of the composition.

The composition may also comprise one or more organic solvents different from the alcohols of formula (I) preferably chosen from alcohols; polyol ethers; $C_5$-$C_{10}$ alkanes; $C_{3-4}$ ketones such as acetone and methyl ethyl ketone; $C_1$-$C_4$ alkyl acetates such as methyl acetate, ethyl acetate and butyl acetate; dimethoxyethane, diethoxyethane; and mixtures thereof.

The composition used in the invention may comprise a propellant. For example, mention may be made of liquefied gases such as dimethyl ether, 1,1-difluoroethane, or $C_{3-5}$ alkanes, for instance propane, isopropane, n-butane, isobutane or pentane, or compressed gases such as air, nitrogen or carbon dioxide, and mixtures thereof.

Mention may be made preferentially of $C_{3-5}$ alkanes and in particular propane, n-butane and isobutane, and mixtures thereof.

When it comprises propellant(s), the composition comprises one or more propellant(s) in an amount ranging from 1% to 60% by weight, better still from 2% to 50% by weight and more preferably still from 4% to 40% by weight relative to the total weight of the composition.

The composition for hair form retention and/or shaping used in the invention may also contain one or more additives selected from fixing polymers, conditioning agents, ceramides and pseudoceramides, vitamins and provitamins including panthenol, sunscreens, pearlescent agents and opacifiers, dyes, sequestrants, plasticizers, solubilizers, acidifying agents, basifying agents, neutralizers, antioxidants, antifoaming agents, moisturizers, emollients, hydroxy acids, penetrants, fragrances, preservatives and solid particles and fillers different from the aerogels, such as for example coloured or colourless mineral and organic pigments.

These additives may be present in the composition used in the invention in an amount ranging from 0 to 20% by weight, relative to the total weight of the composition.

Of course, those skilled in the art will take care to choose the optional additional compounds and/or the amount thereof such that the advantageous properties of the compositions used according to the invention are not, or not substantially, adversely affected by the envisaged addition.

The composition used in the invention may be, inter alia, in the form of liquids that are thickened to a greater or lesser degree, gels, serums, creams, pastes, sprays or mousses.

Preferably, the composition used in the invention is in the form of gels, serums or mousses.

In particular, the composition used in the invention may be applied using an aerosol device.

The cosmetic composition may advantageously be used for the cosmetic treatment of the hair. In particular, the composition may be used for styling the hair, for example for shaping and/or form retention of the hairstyle.

According to one particularly preferred embodiment, the cosmetic composition is used for the simultaneous styling and conditioning of the hair.

The method according to the invention is preferably used for the cosmetic treatment of the hair, for example a hair care method, or a method for shaping and/or form retention of the hairstyle, which comprises the step of applying, to the hair, an effective amount of a composition as described above and then in carrying out an optional rinsing after an optional leave-in time.

Preferably, the composition used in the invention is not rinsed off.

The method of the invention may be carried out at ambient temperature (25° C.) or using heat at a temperature varying from 40° C. to 220° C. using any heating device: hood, hairdryer, tongs.

The invention is illustrated in more detail in the following examples, which are provided by way of illustration and without limitation of the invention.

EXAMPLES

Example 1

Styling Gel Composition

A styling gel was produced with the following ingredients:

| Chemical name | % AM |
| --- | --- |
| Sodium polyacrylate [1] | 1.8 |
| Trimethylated silica [2] | 1.96 |
| 96° ethyl alcohol | 3.724 |
| Propylene glycol | 40 |
| Glycerol | 2 |
| Deionized water | q.s. for 100 |

[1] Covacryl MV 60 (SENSIENT)
[2] Aerogel VM2270 (DOW CORNING)

The gel obtained according to Example 1 is homogeneous and opalescent. It also has a non-greasy feel.

This gel according to Example 1 was applied to wet hair, then left to dry in the open air.

After drying, it was observed that the gel provided the hair with density, a mattifying appearance and volume. The hair furthermore has a pleasant feel which is neither greasy nor dry.

Example 2

Styling Mousse

A styling mousse was produced with the following ingredients:

| Chemical name | % AM |
| --- | --- |
| Absolute ethyl alcohol | 9.5 |
| Propylene glycol | 5.7 |
| Trimethylated silica [2] | 1.3965 |
| Benzyl alcohol | 0.95 |
| D-glucose monohydrate [3] | 2.85 |
| Sodium benzoate | 0.475 |
| Carrageenan powder [4] | 0.95 |
| (85/10/5 C10/C12/C14)Alkyl (1,4) polyglucoside as an aqueous 55% solution[5] | 0.5225 |
| Isobutane/propane/butane mixture | 5 |
| Deionized water | q.s. for 100 |

[2] Aerogel VM2270
[3] Dextrose monohydrate ST
[4] Satiagum UTC 30
[5] Oramix NS 10

The mousse obtained according to Example 2 is homogeneous and opalescent. It also has a non-greasy feel.

This mousse according to Example 2 was applied to wet hair, then left to dry in the open air.

After drying, it was observed that the mousse provided the hair with density, a mattifying appearance and volume. The hair furthermore has a pleasant feel which is neither greasy nor dry.

The invention claimed is:

1. A hair volumizing gel composition comprising:
   an aqueous dispersion of hydrophobic silica silylate aerogel particles,
   a mixture of ethanol and propylene glycol in an amount ranging from about 10% to about 60% by weight, relative to the total weight of the composition,
   sodium polyacrylate in an amount ranging from about 0.2% to about 5% by weight, relative to the total weight of the composition, and
   water in an amount ranging from about 30% to about 80% by weight, relative to the total weight of the composition,
   wherein the composition does not include oil,
   wherein the hydrophobic silica silylate aerogel particles are present in the composition in an amount ranging from 0.5% to 4% by weight, relative to the total weight of the composition, and
   wherein the hydrophobic silica silylate aerogel particles have a specific surface area per unit of mass (SM) ranging from about 600 to about 800 $m^2/g$.

2. A method for volumizing hair, said method comprising applying to the hair an effective amount of a hair volumizing gel composition comprising:
   an aqueous dispersion of hydrophobic silica silylate aerogel particles,
   a mixture of ethanol and propylene glycol in an amount ranging from about 10% to about 60% by weight, relative to the total weight of the composition,
   sodium polyacrylate in an amount ranging from about 0.2% to about 5% by weight, relative to the total weight of the composition, and
   water in an amount ranging from about 30% to about 80% by weight, relative to the total weight of the composition,
   wherein the composition does not include oil,
   wherein the hydrophobic silica silylate aerogel particles are present in the composition in an amount ranging from 0.5% to 4% by weight, relative to the total weight of the composition, and
   wherein the hydrophobic silica silylate aerogel particles have a specific surface area per unit of mass (SM) ranging from about 600 to about 800 $m^2/g$.

* * * * *